United States Patent [19]

McKinlay et al.

[11] Patent Number: 4,957,004
[45] Date of Patent: Sep. 18, 1990

[54] TESTING APPARATUS

[75] Inventors: Peter R. McKinlay; Christos Tseglakoff, both of Victoria, Australia

[73] Assignee: Amcor Limited, S. Melbourne, Australia

[21] Appl. No.: 367,803

[22] Filed: Jun. 19, 1989

[30] Foreign Application Priority Data

Jun. 23, 1988 [AU] Australia ............................... PI8941

[51] Int. Cl.⁵ .............................................. G01N 3/24
[52] U.S. Cl. ....................................................... 73/842
[58] Field of Search .......... 73/823, 827, 831, 833–835, 73/841, 842, 845, 846, 856

[56] References Cited

U.S. PATENT DOCUMENTS

| | | | |
|---|---|---|---|
| 1,298,138 | 3/1919 | Witham Sr. .......................... | 73/835 |
| 2,637,996 | 5/1953 | McKee et al. ....................... | 73/833 |
| 2,982,129 | 5/1961 | Wetzel et al. ....................... | 73/827 |
| 3,678,738 | 7/1972 | Jubelt ................................... | 73/827 |
| 4,297,144 | 10/1981 | Klein et al. ......................... | 106/213 |

OTHER PUBLICATIONS

"The Hunter Terminal Pull Tester", Bulletin 750e, Sept. 1961, Hunter Spring Company, Lansdale, PA.

Primary Examiner—Robert Raevis
Attorney, Agent, or Firm—Bucknam and Archer

[57] ABSTRACT

Modified apparatus for testing the adhesive strength of the bond between the liner and medium in corrugated paperboard in which a clamp is used having a plate 24 abutting one liner and fingers or prongs 21 holding the medium and liner against the plate 24. The bond between the medium and the other liner is measured by applying a force to a strip bonded to the other liner and measuring the applied force which results in failure of the bond. The sample preparation required is simplified with this design which avoids the use of hooks penetrating the sample.

4 Claims, 2 Drawing Sheets

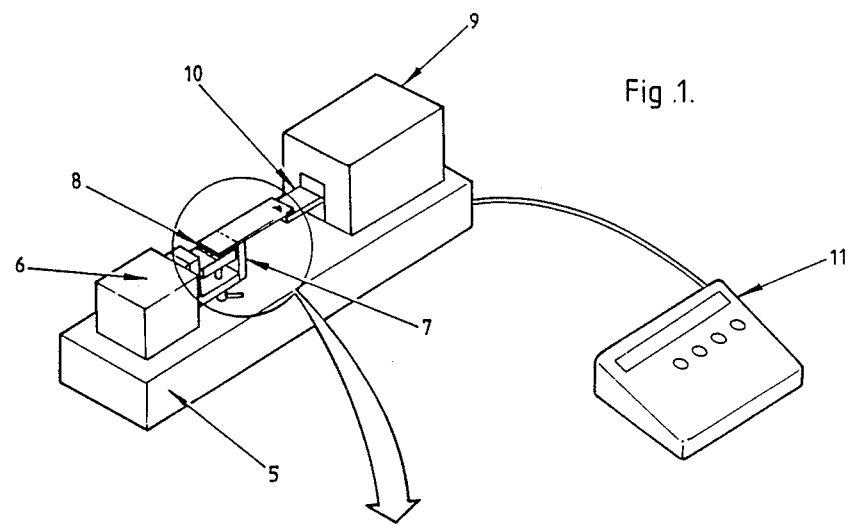
Fig. 1.
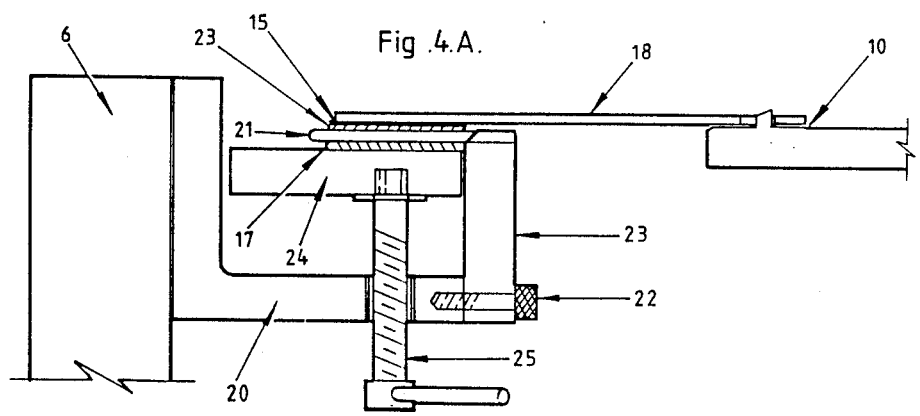
Fig. 4.A.
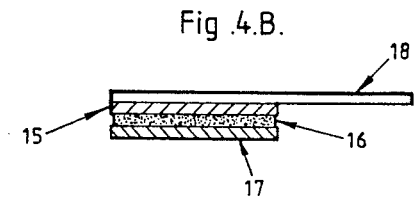
Fig. 4.B.

TESTING APPARATUS

This invention relates to methods of failure testing of materials and in particular corrugated paper board and an apparatus for carrying out the method.

One particular aspect of corrugated board quality control is the quality of the adhesive bond between the lines and the medium, particularly its, resistance to water.

BACKGROUND OF THE INVENTION

Three test methods have been used.

Three standard test is a subjective test of immersion of a sample in water then manual peeling of the liners from the medium and a visual assessment of fibre tear. Absence of fibre tear indicates poor adhesive resistance to water damage.

The FEFCO method No. 9 involves the immersion of a piece of board in water with a specified number of glue bonds subjected to the load imposed by a hanging weight (either 250 or 350 g). The number of hours the bond can withstand the load is measured.

Another more objective method is described in Australian Pat. No. 581511. That patent discloses a technique of preparing a sample of corrugated board by isolating a portion of the outer liner by removing part of the liner to isolate one piece attached to the medium. A hole or eyelet is prepared in the other portion of the board and a plastic strip is hot melt bonded to the portion of liner to be tested.

Hooks are placed in a hole in the plastic strip and the board. The testing apparatus comprises a beam balance with a water collecter on one beam and the sample on the other. The plastic strip is connected to the balance beam while the paperboard sample is secured to the stand. Water is added progressively to the collecter until the wet sample fails and the liner is displaced from the medium. This method aims to apply a constantly increasing force parallel to the glue lines of the sample.

Whilst this test was the first method to produce quantitative results, a number of difficulties exist with this method. The apparatus is clumsy and difficult to control and must be attended by an operator. Sample preparation is tedious and must be carefully done to avoid damage to the medium. The wet sample also tends to tear at the hole in the second portion. Further, if the glue bond of the side to be tested is appreciably stronger than the glue bond in the other side of the sample, then failure occurs on the weaker side rather than on the side to be tested.

SUMMARY OF THE INVENTION

It is an object of this invention to overcome these problems.

The present invention provides a clamp which enables one liner to medium glue bond to be tested whilst firmly securing the medium and other liner. This method specifically loads the glue bond under test and avoids the problem of the sample merely failing at its weakest point.

In particular this invention provides apparatus for testing the strength of the adhesive bond between a corrugated paperboard medium and a liner comprising a load measuring device and a load applying device and connected between them is a means for clamping said medium and a means for securing said liner such that a load is applied to said medium/liner bond in a plane parallel to said adhesive bond.

A sample of board to be tested is carefully cut and the liner adjacent to the glue bond under test is bonded to a plastic strip.

The liner and medium on the opposite side to the glue bond to be tested are securely fixed to the test instrument by a clamping arrangement. The preferred form of clamp comprises a body section projecting from which is a series of prongs adapted to fit within the flutes of the corrugated medium at the appropriate flute pitch and a backing plate loaded against the other face of the liner, and such backing plate is connected to said body section. The backing plate is adjustable to clamp the liner and the glue bond not under test between the prongs and the backing plate.

The plastic strip is then secured to a projecting tongue in the test instrument. This strip is preferably connected to the load applying device while the gripping device for the medium is connected to a load cell as part of the load measuring device.

This arrangement means that a small sample is cut from the board to be tested and no further preparation is required. The sample is effectively tensioned by means of securely holding one liner and the medium bonded to it and applying a shearing force to the other liner.

Another aspect of this invention provides a testing apparatus comprising:

(1) a load cell attached to which a sample clamp as described above opposed to which is;
(2) a second sample clamp secured to a means for applying a progressively increasing force to the glue bond under the test via the plastic strip. The preferred embodiment of this is a projecting lug or other clamping arrangement which attaches to the plastic strip;
(3) a controller for controlling the force applied to the sample by said means; and
(4) a measuring and display device for measuring the force at which displacement and sample failure occur and displaying it.

BRIEF DESCRIPTION OF THE DRAWINGS

A preferred form of ,this invention will now be described in which FIG. 1 is a schematic view of a testing apparatus of this invention.

FIG. 4A is a detailed view of the clamp as shown in FIG. 3 and

FIG. 4B is a side view of the prepared sample.

Figure 2:
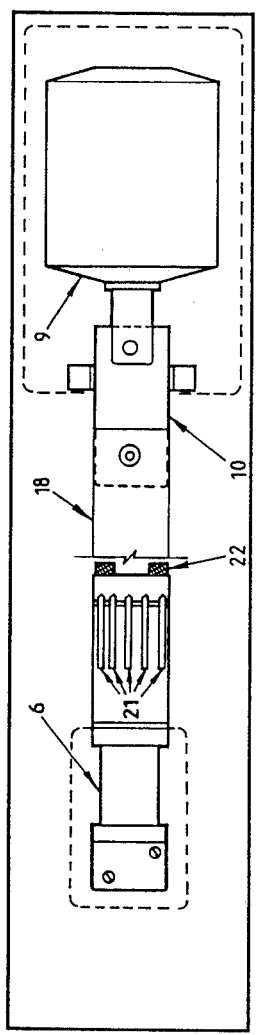
FIG. 2 is a plan view of the apparatus.
Figure 3:
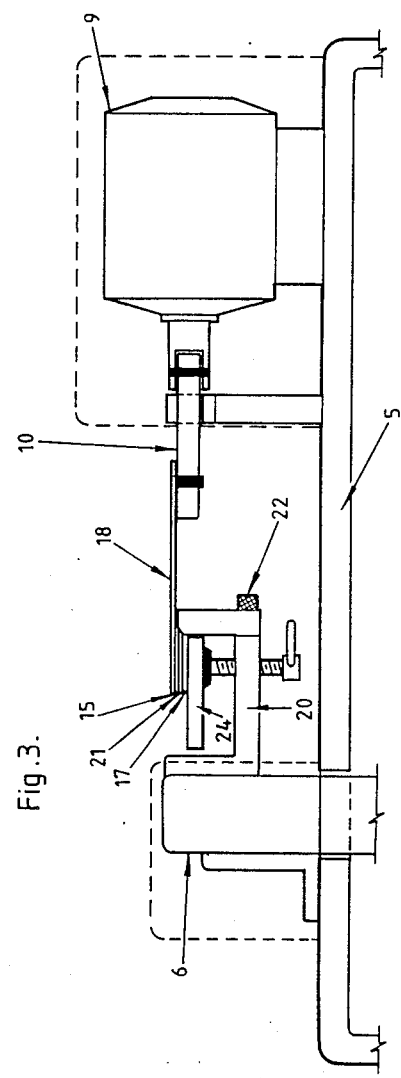
FIG. 3 is a side view of FIG. 2.

The apparatus comprises a body section 5 mounted on which is a load cell 6 secured to which is clamp means 7 and mounted at the other end is the force applying device 9 secured to which is the projecting tongue 10.

The sample 8 is held between the clamp 7 and projecting tongue 10. The controller 11 incorporates a microprocessor and is programmed to provide:

(i) force measurement and control;
(ii) failure detection of sample;
(iii) shear rate input;
(iv) display functions;
(v) a calibration routine;
(vi) statistical processing of results.

The sample 8 best seen in FIG. 4B comprises the topliner 15, the medium 16 and the bottom liner 17.

Liner 15 is bonded preferably by double sided tape to a plastic strip 18. A hole in plastic strip 18 clips into place over the projecting lug on the tongue 10.

The clamp 7 best seen in FIG. 4A comprises a body section 20, a set of prongs 21 which lie on medium 16. These prongs 21 are secured to body section 20 by the screws 22. Plate 24 abuts the outerface of liner 17 so that liner 17 and medium 16 are held between plate 24 and prongs 21. Plate 24 is supported on screw jack 25 which is mounted for threaded movement in body section 20. The screw jack 25 with associated spring ensures the plate 24 is strongly loaded against liner 17. The abutment plate 23 which is part of the body section 20 of clamp 7 is arranged around prongs 21 to prevent any movement of the medium 16 and bottom liner 17.

The avoidance of hooks by using clamp 7 not only avoids tearing of the sample but also enables better sample alignment so that shear force is applied parallel to the flutes and the adhesion lines between the medium and the liner.

From the above it can be seen that the apparatus and sample holder provide a simple and effective means of measuring the wet strength of adhesive bonds in corrugated boards.

We claim:

1. In corrugated paperboard which comprises a corrugated medium with flutes held between a first liner and a second liner, a system for testing the strength of the adhesive bond between said corrugated medium and one first liner, comprising a load measuring device and a load applying device, gripping means connected to said load measuring device for clamping said medium of a sample of said corrugated paperboard, said gripping means comprising a plate and a plurality of prongs adapted to lie within the flutes of the corrugated medium, said sample having been prepared by bonding a rigid strip to the surface of said first liner, said load applying device applying force to said strip bonded to the first liner in a plane parallel to said adhesive bond.

2. The apparatus as claimed in claim 1, wherein said gripping means is connected to said load measuring device and said strip is held by said load applying device.

3. The apparatus according to claim 1, wherein said load applying device has a projecting tongue and said sample is held between said tongue and said gripping means.

4. The apparatus according to claim 1, wherein the strength being measured is the wet strength.

* * * * *

UNITED STATES PATENT AND TRADEMARK OFFICE
CERTIFICATE OF CORRECTION

PATENT NO. : 4,957,004

DATED : SEPTEMBER 18, 1990

INVENTOR(S) : PETER R. McKINLAY and CHRISTOS TSEGLAKOFF

It is certified that error appears in the above-identified patent and that said Letters Patent is hereby corrected as shown below:

On the title page insert:

-(21) Application No. 367,808

Signed and Sealed this

Eleventh Day of August, 1992

Attest:

DOUGLAS B. COMER

Attesting Officer     Acting Commissioner of Patents and Trademarks